US006767553B2

(12) United States Patent
Sun et al.

(10) Patent No.: US 6,767,553 B2
(45) Date of Patent: Jul. 27, 2004

(54) NATURAL FIBERS TREATED WITH ACIDIC ODOR CONTROL/BINDER SYSTEMS

(75) Inventors: Tong Sun, Neenah, WI (US); Sheng-Hsin Hu, Appleton, WI (US); Ronald L. Edens, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/025,386

(22) Filed: Dec. 18, 2001

(65) Prior Publication Data

US 2003/0124171 A1 Jul. 3, 2003

(51) Int. Cl.[7] .......................... A61K 9/70; A61K 9/00; A61L 9/00; A61L 9/01; A01N 25/34
(52) U.S. Cl. ...................... 424/443; 424/400; 424/402; 424/404; 424/76.1
(58) Field of Search ................. 424/76.1, 400, 424/402, 404, 443

(56) References Cited

U.S. PATENT DOCUMENTS

| 2,799,241 A | 7/1957 | Wurster ..................... 118/24 |
| 3,089,824 A | 5/1963 | Wurster ..................... 167/82 |
| 3,117,024 A | 1/1964 | Ross ............................ 118/49 |
| 3,196,827 A | 7/1965 | Wurster et al. ............ 118/24 |
| 3,207,824 A | 9/1965 | Wurster et al. ............ 264/117 |
| 3,241,520 A | 3/1966 | Wurster et al. ............ 118/62 |
| 3,253,944 A | 5/1966 | Wurster ..................... 117/100 |
| 3,338,992 A | 8/1967 | Kinney ....................... 264/24 |
| 3,341,394 A | 9/1967 | Kinney ....................... 161/72 |
| 3,485,706 A | 12/1969 | Evans ......................... 161/72 |
| 3,502,538 A | 3/1970 | Petersen ..................... 161/150 |
| 3,502,763 A | 3/1970 | Hartmann ................... 264/210 |
| 3,534,075 A | 10/1970 | Andress, Jr. ............. 260/404.5 |
| 3,542,615 A | 11/1970 | Dobo et al. ................. 156/181 |
| 3,692,618 A | 9/1972 | Dorschner et al. ........... 161/72 |

(List continued on next page.)

FOREIGN PATENT DOCUMENTS

| AU | 36037 A | 2/2000 | ........... A61L/15/46 |
| DE | 19857547 | 8/2000 | ........... C08L/5/08 |
| DE | 19857548 | 8/2000 | ........... C08L/5/08 |
| EP | 311 344 | 4/1989 | ........... A61L/15/00 |
| EP | 392 528 | 10/1990 | ........... A61L/15/46 |
| EP | 392 607 | 10/1990 | ........... C11D/17/04 |

(List continued on next page.)

OTHER PUBLICATIONS

Dharmawardana, Udeni R. et al.: *A Surface Tension Method for Determining Binding Constants For Cyclodextrin Inclusion Complexes of Ionic Surfactants* (May 1993) (pp. 2258–2263), Institute for Applied Surfactant Research, The University of Oklahoma.

Primary Examiner—Thurman K. Page
Assistant Examiner—Simon J. Oh
(74) Attorney, Agent, or Firm—Pauley Peterson & Erickson

(57) ABSTRACT

A fibrous material, which can be an absorbent material, includes a plurality of natural fibers treated with a carboxylic acid-based odor control agent, which are able to withstand insults with an aqueous liquid without dissolving the odor control agent. The acid-based odor control agent is bound to the natural fibers by an organosilicone polymer binder. The binder is water-insoluble, and can form a highly gas permeable coating. The binder is also highly porous, so as to expose the odor control agent to ammonia and other odoriferous gases which it is intended to control.

43 Claims, 1 Drawing Sheet

U.S. PATENT DOCUMENTS

Figure 1:
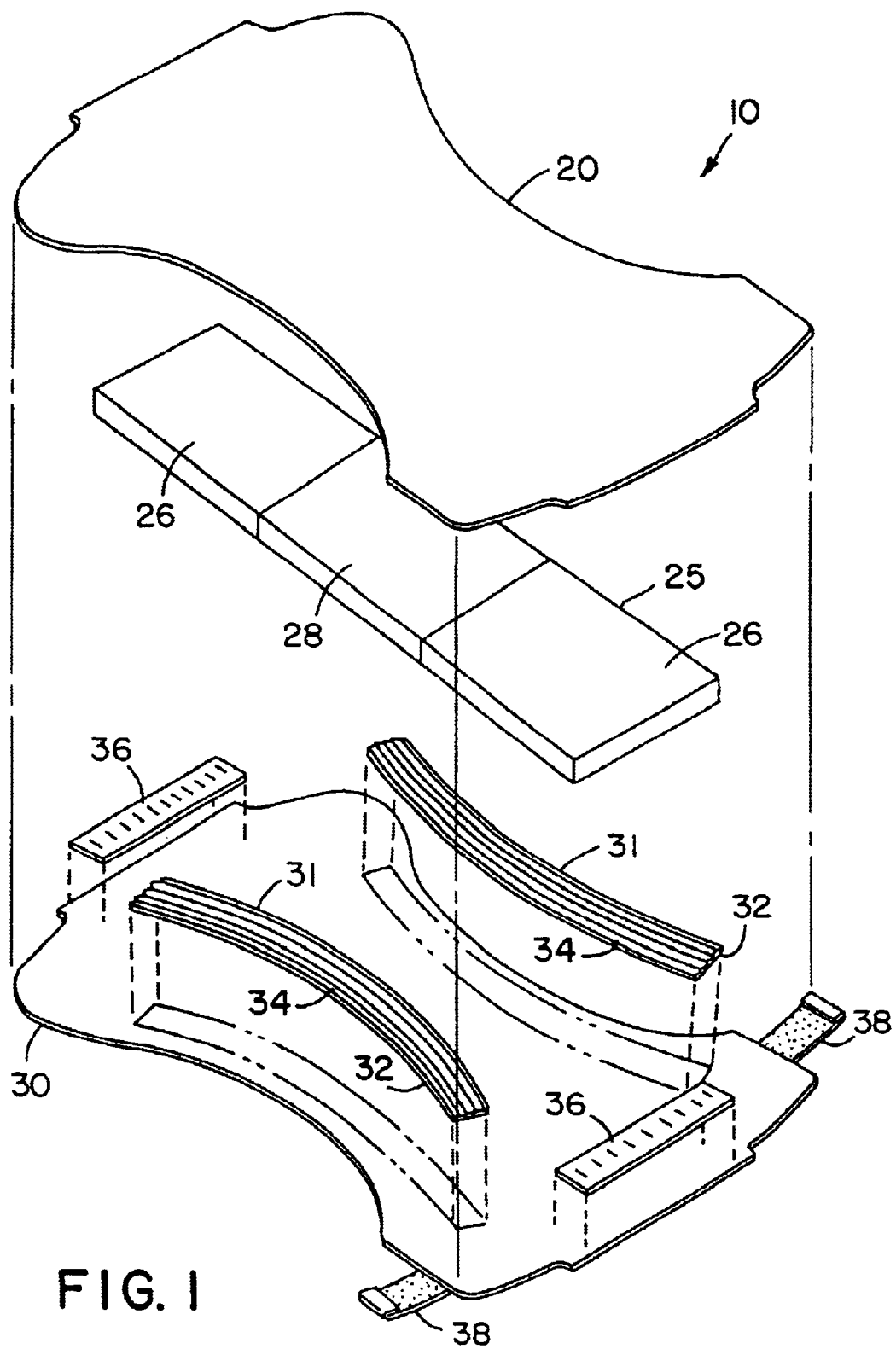

| Patent | | Date | Inventor | Class |
|---|---|---|---|---|
| 3,707,148 | A | 12/1972 | Bryce | 128/284 |
| 3,794,034 | A | 2/1974 | Jones, Sr. | 128/290 |
| 3,802,817 | A | 4/1974 | Matsuki et al. | 425/66 |
| 3,849,241 | A | 11/1974 | Butin et al. | 161/169 |
| 3,855,046 | A | 12/1974 | Hansen et al. | 161/150 |
| 3,879,376 | A | 4/1975 | Vanlerberghe et al. | 260/211 R |
| 3,901,236 | A | 8/1975 | Assarsson et al. | 128/284 |
| 3,903,259 | A | 9/1975 | Hart | 424/76 |
| 3,920,020 | A | 11/1975 | Kraskin | 128/290 |
| 3,953,608 | A | 4/1976 | Vanlerberghe et al. | 424/361 |
| 4,076,663 | A | 2/1978 | Masuda et al. | 260/17.4 GC |
| 4,100,324 | A | 7/1978 | Anderson et al. | 428/288 |
| 4,273,786 | A | 6/1981 | Kraskin | 424/319 |
| 4,286,082 | A | 8/1981 | Tsubakimoto et al. | 526/240 |
| 4,300,561 | A | 11/1981 | Kaczmarzyk et al. | 128/285 |
| 4,340,563 | A | 7/1982 | Appel et al. | 264/518 |
| 4,356,190 | A | 10/1982 | Kraskin | 424/319 |
| 4,377,167 | A | 3/1983 | Kaczmarzyk et al. | 128/285 |
| 4,385,632 | A | 5/1983 | Odelhög | 604/360 |
| 4,479,795 | A | 10/1984 | Mustacich et al. | 604/53 |
| 4,574,150 | A | 3/1986 | Austin | 536/20 |
| 4,617,230 | A | 10/1986 | Shah et al. | 428/288 |
| 4,623,588 | A | 11/1986 | Nuwayser et al. | 428/402.4 |
| 4,638,058 | A | 1/1987 | Brandt et al. | 536/103 |
| 4,675,140 | A | 6/1987 | Sparks et al. | 264/4.3 |
| 4,818,464 | A | 4/1989 | Lau | 264/510 |
| 5,061,792 | A | 10/1991 | Albisetti et al. | 536/20 |
| 5,108,820 | A | 4/1992 | Kaneko et al. | 428/198 |
| 5,161,686 | A | 11/1992 | Weber et al. | 206/440 |
| 5,206,341 | A | 4/1993 | Ibay et al. | 528/361 |
| 5,254,168 | A | 10/1993 | Littman et al. | 118/666 |
| 5,310,865 | A | 5/1994 | Enomoto et al. | 528/361 |
| 5,336,552 | A | 8/1994 | Strack et al. | 428/224 |
| 5,348,667 | A | 9/1994 | Bacon et al. | 252/8.6 |
| 5,382,400 | A | 1/1995 | Pike et al. | 264/168 |
| 5,429,628 | A | 7/1995 | Trinh et al. | 604/359 |
| 5,533,990 | A | 7/1996 | Yeo | 604/363 |
| 5,534,165 | A | 7/1996 | Pilosof et al. | 252/8.91 |
| 5,554,597 | A | 9/1996 | Yu et al. | 514/557 |
| 5,561,158 | A | 10/1996 | Yu et al. | 514/557 |
| 5,571,782 | A | 11/1996 | Trinh et al. | 512/4 |
| 5,578,563 | A | 11/1996 | Trinh et al. | 510/513 |
| 5,591,146 | A | 1/1997 | Hasse | 604/359 |
| 5,593,670 | A | 1/1997 | Trinh et al. | 424/76.1 |
| 5,625,015 | A | 4/1997 | Brinen et al. | 526/160 |
| 5,635,191 | A | 6/1997 | Roe et al. | 424/402 |
| 5,648,067 | A | 7/1997 | Dillenburg et al. | 424/65 |
| 5,663,134 | A | 9/1997 | Trinh et al. | 510/406 |
| 5,668,097 | A | 9/1997 | Trinh et al. | 510/293 |
| 5,670,475 | A | 9/1997 | Trinh et al. | 510/470 |
| 5,690,919 | A | 11/1997 | Rockl et al. | 424/65 |
| 5,698,476 | A | 12/1997 | Johnson et al. | 442/121 |
| 5,714,137 | A | 2/1998 | Trinh et al. | 424/76.4 |
| 5,714,445 | A | 2/1998 | Trinh et al. | 510/103 |
| 5,718,887 | A | 2/1998 | Wolf et al. | 424/65 |
| 5,733,272 | A | 3/1998 | Brunner et al. | 604/359 |
| 5,753,211 | A | 5/1998 | Garson et al. | 424/61 |
| H1732 | H | 6/1998 | Johnson | 428/68 |
| 5,769,833 | A | 6/1998 | Hasse | 604/359 |
| 5,770,711 | A | 6/1998 | Greene et al. | 536/18.6 |
| 5,780,020 | A | 7/1998 | Peterson et al. | 424/65 |
| 5,785,697 | A | 7/1998 | Trombetta et al. | 604/378 |
| 5,821,215 | A | 10/1998 | Crudden et al. | 510/392 |
| 5,865,792 | A | 2/1999 | Ledger et al. | 604/20 |
| 5,871,718 | A | 2/1999 | Lucas et al. | 424/65 |
| 5,871,719 | A | 2/1999 | Lucas et al. | 424/65 |
| 5,874,164 | A | * 2/1999 | Caldwell | 428/306.6 |
| 5,928,631 | A | 7/1999 | Lucas et al. | 424/65 |
| 5,932,495 | A | 8/1999 | Boney et al. | 442/121 |
| 5,942,217 | A | 8/1999 | Woo et al. | 424/76.1 |
| 5,955,093 | A | 9/1999 | Woo et al. | 424/401 |
| 5,961,996 | A | 10/1999 | Garson et al. | 424/401 |
| 5,968,404 | A | 10/1999 | Trinh et al. | 252/8.91 |
| 5,997,759 | A | 12/1999 | Trinh et al. | 252/8.91 |
| 5,998,511 | A | 12/1999 | Westland et al. | 524/13 |
| 6,001,343 | A | 12/1999 | Trinh et al. | 424/76.4 |
| 6,031,147 | A | 2/2000 | Gross | 604/359 |
| 6,033,486 | A | 3/2000 | Andros | 134/6 |
| 6,033,679 | A | 3/2000 | Woo et al. | 424/401 |
| 6,066,673 | A | 5/2000 | McIver et al. | 514/634 |
| 6,100,233 | A | 8/2000 | Sivik et al. | 512/26 |
| 6,106,738 | A | 8/2000 | Woo et al. | 252/8.91 |
| 6,114,496 | A | 9/2000 | Otera et al. | 528/361 |
| 6,156,296 | A | 12/2000 | Riedel et al. | 424/70.1 |
| 6,190,694 | B1 | 2/2001 | Mizushima et al. | 424/451 |
| 6,229,062 | B1 | 5/2001 | Mandell et al. | 604/367 |

FOREIGN PATENT DOCUMENTS

| | | | | |
|---|---|---|---|---|
| EP | 392 608 | | 10/1990 | C08B/37/16 |
| EP | 510 619 | | 10/1992 | A61F/13/15 |
| EP | 562 620 | | 9/1993 | A61L/15/46 |
| EP | 685 213 | | 12/1995 | A61F/13/15 |
| EP | 811 390 | | 12/1997 | A61L/15/46 |
| EP | 811 391 | | 12/1997 | A61L/15/46 |
| EP | 813 848 | | 12/1997 | A61F/13/15 |
| EP | 953 589 | | 11/1999 | C08G/63/80 |
| JP | 01-005553 | | 1/1989 | A61L/09/01 |
| JP | 1-104885 | | 4/1989 | D06M/15/564 |
| JP | 02-190187 | | 7/1990 | C12N/11/14 |
| JP | 03-109351 | | 5/1991 | C07C/69/675 |
| JP | 2771863 | | 7/1998 | C07C/69/675 |
| JP | 1-104885 | A * | 4/1999 | D06M/15/564 |
| JP | 3042691 | B2 | 5/2000 | C12N/11/14 |
| WO | 22500 | | 10/1994 | A61L/15/46 |
| WO | 17175 | | 6/1995 | A61K/9/70 |
| WO | 04937 | | 2/1996 | A61L/9/01 |
| WO | 05358 | | 2/1996 | D06M/15/11 |
| WO | 24318 | | 8/1996 | A61F/13/15 |
| WO | 07455 | | 2/1998 | A61L/9/01 |
| WO | 17239 | | 4/1998 | A61K/7/32 |
| WO | 17240 | | 4/1998 | A61K/7/32 |
| WO | 18439 | | 5/1998 | A61K/7/32 |
| WO | 26808 | | 6/1998 | A61L/9/01 |
| WO | 99/61518 | | 2/1999 | C08J/9/00 |
| WO | 99/32697 | | 7/1999 | D06M/15/03 |
| WO | 45973 | | 9/1999 | A61L/15/44 |
| WO | 45974 | | 9/1999 | A61L/15/44 |
| WO | 99/45976 | | 9/1999 | A61L/15/46 |
| WO | 55814 | | 11/1999 | C11D/3/22 |
| WO | WO 99/61518 | * | 12/1999 | C08J/9/00 |
| WO | 10500 | | 3/2000 | A61F/13/15 |
| WO | 00/50098 | | 8/2000 | A61L/15/48 |
| WO | 62826 | | 10/2000 | A61L/15/18 |
| WO | 01/32226 | | 5/2001 | A61L/15/20 |

* cited by examiner

NATURAL FIBERS TREATED WITH ACIDIC ODOR CONTROL/BINDER SYSTEMS

FIELD OF THE INVENTION

This invention relates to natural fibers, desirably absorbent fibers such as cellulose fibers, which are treated with acidic odor control agent/binder systems. The treated fibers are useful in the absorbent cores of personal care absorbent articles, medical absorbent articles and the like.

BACKGROUND OF THE INVENTION

For many personal care absorbent articles, medical absorbent articles, and the like, it is desirable to reduce, prevent, or eliminate odors during use. For diapers and other incontinence products, it is desirable to reduce or eliminate the odor of ammonia which is present in urine. For feminine hygiene products, it is desirable to reduce or eliminate the odors of trimethylamine and triethylamine. Other common odor-producing substances include isovaleric acid, dimethyl disulfide, and dimethyl trisulfide.

Odor control agents include odor inhibitors, odor absorbers, odor adsorbers and other compounds which suppress odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.

Acidic odor control agents based on carboxylic acids and their derivatives are used to neutralize or inhibit formation of odors from ammonia and other basic odor-forming compounds. Ammonia, released from aqueous ammonium hydroxide, is one of the primary odor-producing substances in urine. One of the drawbacks of acidic odor control agents is they are not inherently durable, i.e., they pass into solution after one or more insults with aqueous liquid, and may acidify the liquid. If some of the acidified aqueous liquid leaks from the absorbent article and passes to the wearer's skin, the wearer may experience itching, rash, and/or other uncomfortable effects.

Previously, acidic odor control agents have been applied to absorbent articles in the form of powders, coatings, and the like, which can be easily dissolved away. There is a need or desire for absorbent articles having durable acidic odor control agents, which retain their odor control functions and do not pass into solution after one or more insults with aqueous liquid.

DEFINITIONS

The term "cellulose fibers" refers to fibers from wood, paper, woody plants, and certain non-woody plants. Woody plants include, for example, deciduous and coniferous trees. Non-woody plants include, for instance, cotton, flax, esparto grass, milkweed, straw, jute hemp, and bagasse.

The term "natural fibers" includes cellulose fibers, carbon fibers, and other fibers existing in nature, as well as modifications of such fibers (for instance, treated cellulose fibers, activated carbon fibers, and the like).

The term "average fiber length" refers to a weighted average length of fibers determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_i * n_i)/n$$

where
  k=maximum fiber length,
  $X_i$=individual fiber length,
  $n_1$=number of fibers having length $X_i$
and
  n=total number of fibers measured.

The term "carboxylic acid-based odor control agent" includes odor control agents based on carboxylic acids and/or their partially neutralized salts. The term "multicarboxylic acid-based odor control agent" includes odor control agents based on dicarboxylic acids, tricarboxylic acids, polycarboxylic acids, etc., having two or more carboxylic acid groups, and/or their partially neutralized salts.

The term "polymeric polycarboxylic acid" refers to a polymer having multiple carboxylic acid groups in its repeating units. Examples include polyacrylic acid polymers, polymaleic acid polymers, copolymers of acrylic acid, copolymers of maleric acid, and combinations thereof. Other examples are disclosed in U.S. Pat. No. 5,998,511, which is incorporated by reference.

The term "odor control system" refers collectively to individual odor control agents, and combinations (by chemical reaction and/or blending) of two or more odor control agents.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "personal care absorbent product" includes without limitation diapers, training pants, swim wear, absorbent underpants, baby wipes, adult incontinence products, and feminine hygiene products.

The term "medical absorbent product" includes without limitation garments, underpads, bandages, absorbent drapes, and medical wipes.

The term "absorbent fibers" refers to fibers capable of absorbing about 5 to less than 15 times their weight in an aqueous solution containing 0.9 weight percent sodium chloride. The term is intended to include cellulose fibers, but not superabsorbent materials.

"Superabsorbent" or "superabsorbent material" refers to a water-swellable, water-insoluble organic or inorganic material capable, under the most favorable conditions, of absorbing at least about 15 times its weight and, more desirably, at least about 20 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

The terms "silicone polymer," "polyorganosiloxane" and "polysiloxane" interchangeably refer to siloxane polymers based on a structure of alternating silicon and oxygen atoms with various organic radicals attached to the silicon:

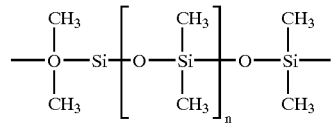

The term "odor control system" refers collectively to individual odor control agents, and combinations (by chemical reaction and/or blending) of two or more odor control agents.

SUMMARY OF THE INVENTION

The present invention is directed to natural fibers including cellulose, activated carbon or the like, treated with a combination of odor control system and binder, where the odor control system includes a carboxylic acid odor control agent and the binder includes a polyorganosiloxane (i.e., silicone polymer). The inventors have found that silicone polymers serve as excellent binders between carboxylic odor control agents (and systems containing them) and the natural fibers. The silicone polymers have a unique ability to protect the acidic odor control agents from being dissolved or otherwise passed into solution by aqueous liquids, while at the same time permitting odoriferous gases such as ammonia to reach the odor control agents. Put another way, the silicone polymers are water insoluble, and at the same time are highly porous.

In one embodiment of the invention, the odor control system and silicone polymer are combined together, with the silicone polymer being in a molten form or dissolved or suspended in a solvent. The combination of odor control system and silicone polymer are applied to the natural fibers, desirably absorbent fibers such as cellulose, by spray coating, brushing, printing, dipping, extrusion, or the like.

In another embodiment of the invention, the odor control system is first applied to the natural fibers using spray coating, brushing, printing, dipping, extrusion, or the like. The silicone polymer is then applied to the natural fibers over the odor control agent using spray coating, brushing, printing, dipping, extrusion, or the like.

In one embodiment of the invention, the odor control system includes activated carbon fibers in addition to the carboxylic acid odor control agent. The silicone polymer, other natural fibers (e.g., cellulose fibers) and carbon fibers can be combined using any foregoing technique. The silicone polymer binds to the activated carbon fibers as well as to the cellulose or other natural fibers to form an integrated odor control/binder system.

In another embodiment of the invention, the odor control system includes a multi-carboxylic acid-modified chitin or chitosan complex odor control agent. The carboxyl sites facilitate absorption of ammonia and amine-based odors. The amino groups on the chitin or chitosan facilitate absorption of acid-based odor compounds, and suppress the enzymatic decomposition of urine and menses, thereby inhibiting odor generation. This odor control system can also be combined with activated carbon to provide additional control of amino, sulfuric and acidic odors.

DETAILED DESCRIPTION OF THE PRESENTLY PREFERRED EMBODIMENTS

In accordance with the invention, an odor control system including an acidic odor control agent is used in conjunction with a silicone polymer binder to provide a natural fiber material with the ability to control odors from aqueous ammonia and other basic odoriferous compounds, and to maintain the ability to control odor after one or more aqueous liquid insults.

The natural fiber material can be an absorbent material, made using cellulose fibers. The natural fiber material may also be another odor control agent, such as activated carbon, or a combination of cellulose and activated carbon fibers or particles. The treated natural fiber material can be used in a wide variety of personal care products and medical products, and in other applications.

The natural fibers may have high average fiber lengths, low average fiber lengths, or may be a combination of high and low average fiber length fibers. High average fiber length fibers generally have an average fiber length greater than about 1.5 mm, suitably about 1.5–6 mm, when measured using an optical fiber analyzer such as the Kajaani tester described above. Low average fiber length fibers generally have an average fiber length less than about 1.5 mm, suitably about 0.7–1.2 mm, when measured using an optical fiber analyzer such as the Kajaani tester. Cellulose fibers from any source, and/or activated carbon fibers, are suitable for use in the invention. Fibers from wood, paper and the like, are particularly suitable.

The odor control system includes at least one acidic odor control agent, desirably a carboxylic acid-based odor control agent. Suitable carboxylic acid odor control agents include without limitation hydroxycarboxylic acids such as citric acid, malic acid, tartaric acid, and the like. Other suitable carboxylic acid odor control agents include without limitation formic acid, acetic acid, propionic acid, butyric acid, isobutyric acid, pyruvic acid, glycolic acid, lactic acid, and combinations thereof.

The acidic odor control agent may be combined (i.e., mixed or reacted) with one or more compatible odor-control agents to provide enhanced odor control properties. For instance a hydroxy carboxylic odor control agent, or another multi-carboxylic acid odor control agent, may be combined with chitin or chitosan. This can be accomplished by blending a calculated amount of chitin and/or chitosan with a calculated amount of an aqueous solution of the multi-carboxylic acid odor control agent at room temperature for 30 minutes, and then drying the mixture in an oven at 50° C. for eight hours. The acid concentration in the starting aqueous solution is desirably in the range of about 5–55% by weight. The degree of diacetylation in the chitosan should be determined before adding chitosan to the acid solution. The amount of chitosan added to the acid solution should be selected so that the molar equivalent ratio of free amino groups in the chitosan to free carboxyl groups in the multi-carboxylic acid is about 0.2–0.4. The resulting odor control system is useful in absorbing, neutralizing, and inhibiting formation of ammonia, trimethylamine, isovaleric acid, and similar odoriferous compounds. In this embodiment, the acid is suitably citric acid, malic acid or tartaric acid, and is desirably citric acid.

A multi-carboxylic acid odor control agent may also be combined with a metal-oxide, suitably zinc oxide, to adjust the pH of the odor control agent by partially converting the free acid groups to their metallic salts. Other suitable metal oxides include transition metals such as cadmium, zirconium, chromium, copper, and the like. This partial neutralization of the multi-carboxylic acid can render it more useful for treating layer materials which contact the human body. The resulting odor control system is useful in absorbing, neutralizing, and inhibiting formation of ammonia, trimethylamine, isovaleric acid, and similar odoriferous compounds. In this embodiment, the acid is suitably citric acid, malic acid or tartaric acid, and is desirably citric acid.

The acidic odor control agent may also be a chelating agent. Suitable chelating agents include without limitation aminopolycarboxylic acids, their alkali metal salts, and combinations thereof Suitable aminopolycarboxylic acids and alkali metal (preferably sodium) salts thereof, include without limitation ethylenediamine tetraacetic acid (EDTA), the alkali metal salts of EDTA (for instance, $Na_2$ EDTA, $Na_3$ EDTA, and $Na_4$ EDTA), nitrilotriacetic acid, the alkali metal (e.g., sodium) salts of cyclohexanediamine tetraacetic acid, diethylenetriamine pentaacetic acid (DTPA), hydroxyethyl-enediamine triacetic acid (HEDTA), pentasodium diethyl-enetriamine pentaacetate, trisodium hydroxyethyl ethylene-diamine triacetate, and combinations thereof. A particularly suitable aminopolycarboxylic acid is EDTA. Suitable chelating agents also include polyamino disuccinic acids and alkali metal salts of them, including acids and salts of ethylenediamine-N,N'-disuccinic acid, diethylenetriamine-N,N''-disuccinic acid, triethylenetetraamine-N,N'''-disuccinic acid, 1,6-hexamethylenediamine N,N-disuccinic acid, tetraethylenepentaamine-N,N''''-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, cis-cyclohexanediamine-N,N'-disuccinic acid, trans-cyclohexanediamine-N,N'-disuccinic acid, and ethylene-bis (oxyethylenenitrilo)-N,N'-disuccinic acid. One suitable polyamino disuccinic acid is ethylenediamine-N,N'-disuccinic acid. Chelating agents can act as odor inhibitors which prevent odor from occurring by interfering with reactions that produce odors, as well as odor absorbents which remove or minimize existing odor-producing compounds.

In another embodiment of the invention, activated carbon fibers can also be added to the odor control system. Activated carbon helps to prevent or reduce various odors such as triethylamine, trimethylamine, dimethyl disulfide, and isovaleric acid, but does not alone neutralize ammonia odor. By combining activated carbon fibers with the multicarboxylic-acid based odor control agents and combinations described above, an order control system can be devised which prevents and/or reduces a wide variety of odors. In this embodiment, the silicone polymer binder described below serves dual purposes of a) binding the acid-based odor control agents and combinations described above to the absorbent (e.g., cellulose) fibers, and b) binding the activated carbon to the acid-based odor control agents and combinations, and/or to the absorbent fibers.

The binder includes a polyorganosiloxane (i.e., a silicone polymer). As described above, a silicone polymer contains a repeating silicon-oxygen backbone and has organic groups "R" attached to a significant portion of the silicon atoms by silicon-carbon bonds. Suitable "R" groups include, without limitation, methyl, longer alkyl, fluoroalkyl, phenyl, vinyl and the like. Specific silicone polymers include, without limitation, poly(hexamethyldisiloxane), poly (octamethyltrisiloxane), poly(decamethyltetrasiloxane), poly(octamethylcyclotetrasiloxane), poly (octaphenylcyclotetrasiloxane), and combinations thereof. Silicone polymers may be in the form of homopolymers, random copolymers, block copolymers, and combinations thereof. Preferred silicone polymers vary with the method of application to the fibrous material. Silicone polymers having higher melting points are suitable for extrusion. Silicone polymers having lower melting points are suitable for application by spraying, dipping, and the like.

The amount of silicone polymer binder should be sufficient to effectively bind the odor control system to the fibrous material, but not so high as to unnecessarily inhibit the odor control performance. Generally, the silicone polymer should be present in an amount of about 5 to 200 parts by weight silicone polymer per 100 parts by weight of dry, water-free, solvent-free odor control system. Suitably, the silicone polymer should be present in an amount of about 10 to 100 parts by weight silicone polymer per 100 parts by weight dry odor control system, desirably in an amount of about 15 to 50 parts by weight silicone polymer per 100 parts by weight of dry odor control system. Exemplary silicone polymers which are particularly suitable as binding agents include Dow Corning® 84 Additive, Dow Corning® 36 emulsion, and Dow Corning® Q2-3195.

In one embodiment of the invention, the odor control system may also include a particulate inorganic material, such as a pigment and/or filler. Particulate materials such as titanium dioxide, clay, calcium carbonate and/or silica can be added at 0.01–5% by weight, desirably 0.1–1.0% by weight of the odor control system. In addition to providing pigment, these materials contribute to porosity of the silicone polymer binder. One suitable pigment is KEMIRA® UDR-P, available from Kemira Pigment Co. of Savannah, Ga.

The silicone polymer can be combined with the odor control system before the combination is applied to the natural fibers. A wide variety of blending techniques can be used to combine the ingredients, including without limitation melt blending, solution mixing, spray drying, fluidized bed coating, and the like. By way of example, an odor control agent including citric acid can be dissolved in water, suitably at a concentration of about 0.1–15% by weight citric acid. A calculated amount of zinc oxide can then be stirred into the acid solution to partially neutralize the free acid groups to their metallic salts, effecting a solution pH of about 4.5. Then, silicone polymer sold as Dow Corning® 84 Additive by the Dow Corning Corporation can be added to the citric acid/zinc oxide solution in an amount of about 0.1–0.75 parts by weight silicone polymer per part by weight dry citric acid/zinc oxide system. Then, the combined silicone polymer/odor control system can be applied to a natural fiber substrate, such as a fibrous cellulose web, using spray drying, fluidized bed coating, a rotating spray coating process, or another suitable technique. Additionally, titanium dioxide pigment may be added, for example, at up to about 0.75 parts by weight pigment per part by weight citric acid/zinc oxide system.

Alternatively, the silicone polymer can be combined with the odor control system after, or at the same time, that the odor control system is applied to the natural fiber substrate. A wide variety of techniques can be used to apply both the odor control system and the silicone polymer binder to the substrate, including without limitation melt extrusion, printing, dipping, coating, brushing, and the like. By way of example, an aqueous odor control agent containing a hydroxycarboxylic acid can be applied in powder form to a fluidized bed. A fibrous substrate, such as a collection of absorbent cellulose fibers, can be charged to the fluidized bed along with a suitable amount of chitosan for the odor control system. Simultaneously, a liquid silicone polymer sold as Dow Corning® 84 Additive by the Dow Corning Corporation can be sprayed through a nozzle located at the center of the fluidized bed. The silicone polymer and powdered odor control system (including chitosan and hydroxycarboxylic acid) will accordingly attach to the natural fiber substrate, and to each other. Where activated carbon is used as part of the odor control system, the carbon particles or fibers can also be coated with the silicone polymer binder using the fluidized bed.

A wide variety of fluidized bed coating systems can be adapted to coat absorbent cellulose fibers and/or activated carbon particles with a silicone polymer binder. For example, one can use a Wurster Fluid Bed Coater such as the Ascoat Unit Model 101 of Lasko Co. (Leominster, Mass.), the Magnacoater® by Fluid Air, Inc. (Aurora, Ill.), or the modified Wurster coater described in U.S. Pat. No. 5,625,015, issued Apr. 29, 1997 to Brinen et al., herein incorporated by reference. The coater is typically configured as a cylindrical or tapered vessel (larger diameter at the top than at the bottom) with air injection at the bottom through air jets or a distributor plate having multiple injection holes. Fibers and/or particles are fluidized in the gaseous flow. One or more spray nozzles inject the silicone polymer coating material initially provided as a liquid slurry, or foam at a point where a good contact with the moving fibers and/or particles can be achieved. The fibers and/or particles move upwards and descend behind a wall or barrier, from whence they can be guided to again enter the fluidized bed and be coated again, or can be removed and further processed. Elevated air temperature or the application of other forms of energy (microwaves, infrared radiation, electron beams, ultraviolet radiation, steam, and the like) causes drying or curing of the silicone polymer coating material on the fibers and/or particles. The fibers and/or particles can be recycled through the fluidized bed a plurality of times to provide the desired amount of the silicone polymer binder coating.

The original Wurster fluid bed coaters are described in U.S. Pat. No. 2,799,241, issued Jul. 16, 1957 to D. E. Wurster; U.S. Pat. No. 3,089,824, issued May 14, 1963 to D. E. Wurster; U.S. Pat. No. 3,117,024, issued Jan. 7, 1964 to J. A. Lindlof et al.; U.S. Pat. No. 3,196,827, issued Jul. 27, 1965 to D. E. Wurster and J. A. Lindlof; U.S. Pat. No. 3,207,824, issued Sep. 21, 1965 to D. E. Wurster et al.; U.S. Pat. No. 3,241,520 issued Mar. 21, 1966 to D. E. Wurster and J. A. Lindlof; and U.S. Pat. No. 3,253,944, issued May 31, 1966 to D. E. Wurster; all of which are herein incorporated by reference. More recent examples of the use of Wurster coaters are given in U.S. Pat. No. 4,623,588, issued Nov. 18, 1986 to Nuwayser et al., herein incorporated by reference. A related device is the coater of H. Littman disclosed in U.S. Pat. No. 5,254,168, "Coating Apparatus Having Opposed Atomizing Nozzles in a Fluid Bed Column," issued Oct. 19, 1993, herein incorporated by reference.

Other coating methods need not rely on fiber and/or particle fluidization in a gas stream. Fibers and/or particles can be sprayed or treated with a coating material while being mechanically agitated by a shaker or other pulsating device, while falling from one container to another, while tumbling in a moving vessel or a vessel with rotating paddles such as a Forberg coater (Forberg A S, Larvik, Norway) which can be operated without applied vacuum to keep the coating material on the surface of the fibers and/or particles, or while resting in a bed, after which the fibers and/or particles are separated or broken up. In one embodiment, fibers and/or particles and a coating liquid or slurry are first combined and then separated into individually coated fibers and/or particles by centrifugal forces, as disclosed in U.S. Pat. No. 4,675,140, issued Jun. 23, 1987 to Sparks et al., herein incorporated by reference. Systems for coating dry fibers and/or particles can also be adapted for coating according to the present invention.

The amount of odor control system needed for application to the natural fibers will vary depending on the type of odor control agents in the system, the amount and type of odor(s) being controlled, the amount and type of silicone polymer binder, and other factors. On a dry weight basis, the odor control system should generally constitute about 0.1–50% by weight of the natural fibers to which it is applied, suitably about 0.5–30% by weight, desirably about 2–15% by weight. The treated natural fibers may also be blended with untreated fibers in any desired amount.

The treated natural fibers thus formed (alone or in combination with untreated fibers) can be used in a wide variety of absorbent product applications including, in particular, personal care absorbent products. Personal care absorbent products include diapers, training pants, swim wear, absorbent underpants, baby wipes, adult incontinence products, feminine hygiene products, and the like. In absorbent products, the treated natural fibers (if absorbent) can be used in an absorbent core or other absorbent composite capable of absorbing aqueous liquids. An absorbent composite may include, for instance, treated cellulose fibers alone or in combination with untreated cellulose fibers and/or a superabsorbent material. The treated natural fibers can also be used in medical absorbent products, including without limitation garments, underpads, absorbent drapes, bandages, and medical wipes. Other uses include air filters, water filters, industrial wipes, poultry pads and bed pads.

By way of example, FIG. 1 is an exploded perspective view of a disposable diaper according to one embodiment of this invention. Referring to FIG. 1, disposable diaper 10 includes outer cover 30, body-side liner 20, and absorbent core 25 between body-side liner 15 and outer cover 12. Body-side liner 20 and outer cover 30 are constructed of conventional non-absorbent materials. By "non-absorbent" it is meant that these materials have an absorptive capacity of less than 5 grams of 0.9% aqueous sodium chloride solution per gram of material. INDA Standard Test Method IST 10.1 (95), "Standard Test Method for Absorbency Time, Absorbency Capacity, and Wicking Time," published by INDA, Association of the Nonwoven Fabrics Industry, Cary, N.C., provides the basis for a suitable test method to measure absorbency, and is incorporated by reference.

Body-side liner (topsheet) 20 is constructed from highly liquid pervious materials. Body-side liner 20 functions to allow liquid from the wearer to contact the absorbent material or superabsorbent material present in diaper 10. Body-side liner 20 can be made from materials including porous woven materials, porous nonwoven materials, films with apertures, open-celled foams, and batting.

Additionally, a surge layer (not shown) made from nonwoven fibers can be added between body-side liner 20 and absorbent core 25. The surge layer includes surge material having an operable level of density and basis weight to quickly collect and temporarily hold liquid surges, to transport the liquid from its initial entrance point and to substantially release the liquid to absorbent core 25 and the superabsorbent material in absorbent core 25.

One embodiment of diaper 10 includes a barrier tissue between body-side liner 20 and absorbent core 25. Alternatively, the barrier tissue may be between a surge layer and body-side liner 20 or between the surge layer and absorbent core 25. A barrier tissue is beneficial in keeping any loosened superabsorbent material from passing through body-side liner 20 and contacting the user. Barrier tissues are typically natural fiber materials such as any type of wood pulp. Barrier tissues can also be made from uncreped through air-dried (UCTAD) tissue material known in the art.

Outer cover material (backsheet) 30 should be breathable to water vapor. Outer cover 30 desirably includes a material that is substantially liquid impermeable, and can be elastic, stretchable or nonstretchable. The outer cover 30 can be a single layer of liquid impermeable material, but desirably includes a multi-layered laminate structure in which at least one of the layers is liquid impermeable. For instance, the outer cover 30 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 15 is made. While it is not a necessity for the outer layer to be liquid permeable, it is desired that it provides a relatively cloth-like texture to the wearer.

The inner layer of the outer cover 30 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 30 when a single layer, prevents waste material from wetting articles, such as bedsheets and clothing, as well as the wearer and care giver. A suitable liquid impermeable film for use as a liquid impermeable inner layer, or a single layer liquid impermeable outer cover 30, is a 0.2 millimeter polyethylene film commercially available from Huntsman Packaging of Newport News, Va., U.S.A. If the outer cover 30 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 30. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

Generally outer cover 30 will have a moisture vapor transmission rate (MVTR) of at least about 300 grams/$m^{2-24}$ hours, preferably at least about 1000 grams/$m^{2-24}$ hours, more preferably at least about 3000 grams/$m^{2-24}$ hours, measured using INDA Test Method IST-70.4-99, herein incorporated by reference.

Attached to outer cover 30 are waist elastic members 36, fastening tapes 38 and leg elastic members 31. The leg elastics 31 include a carrier sheet 32, which can be a polyolefin film, and individual elastic strands 34. The waist elastic members 36 and the leg elastic members 31 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 31 include a plurality of dry-spun coalesced multifilament spandex elastomeric threads sold under the trade name LYCRA® and available from E. I. DuPont de Nemours and Company, Wilmington, Del., U.S.A.

The diaper of FIG. 1 is a general representation of one basic diaper embodiment. Various modifications can be made to the design and materials of diaper parts. The various layers of article 10 have dimensions which vary depending on the size, shape, and needs of the wearer.

Absorbent core 25 typically includes absorbent materials including natural fibers such as wood pulp fibers. The treated cellulose fibers of the invention may be used in place of untreated natural fibers, or may be combined with untreated natural fibers in any desired ratio. Absorbent core 25 can also include nonwoven fibers or webs. "Nonwoven" and "nonwoven web" refer to materials and webs of material which are formed without the aid of a textile weaving or knitting process. Absorbent core 25 typically includes a matrix of hydrophilic fibers, such as a web of cellulosic fluff, mixed with particles of a superabsorbent material. In a particular embodiment, absorbent core 25 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. Examples of fiber materials used in absorbent core 25 include, without limitation, wood pulp fluff, cotton, wool, silk, polyethylene, polypropylene, polyester, nylon, polyvinyl alcohol, polyacrylonitrile, and polyvinyl chloride.

The superabsorbent material can be in the form of fibers, particles, filaments, or printed or coated onto the cellulose fiber matrix. Any conventional superabsorbent material can be used. The superabsorbent material can be substantially homogeneously mixed with the hydrophilic cellulose matrix or can be nonuniformly mixed. The cellulose and superabsorbent particles can also be selectively placed into desired regions of the absorbent core 25 to better contain and absorb body exudates. The concentration of the superabsorbent particles can also vary through the thickness of the absorbent core 25. Alternatively, absorbent core 25 can include a laminate of fibrous webs and superabsorbent material or other suitable means of maintaining a superabsorbent material in a localized area.

EXAMPLES

Example 1

This example relates to the coating of absorbent cellulose fibers with an odor control system including chitosan and a hydroxycarboxylic acid, using a silicone polymer binder. The chitosan/HCA was prepared using chitosan VNS-608 purchased from Varson Company in Redmond, Va. Chitosan VNS-608 has a Brookefield viscosity of 11,400 centipoise (for a 1% solution in 1% acetic acid) and has a degree of acetylation of 86%. 190 grams of chitosan VNS-608 flakes was mixed with 295 ml deionized water in a mixer. The suspension was stirred at ambient temperature for 1.5 hours. Then, to prepare the chitosan/HCA, a mixture of 128 grams anhydrous citric acid (available from Aldrich Co. in Milwaukee, Wis.) and 200 ml deionized water was added into the chitosan-water slurry with stirring. After a thorough stirring, the blend was poured onto the Teflon-lined trays, and dried in a convection oven at 50° C. The dried citosan/HCA product was ground using a Waring blender and sieved, yielding particles having sizes between 100 and 300 microns.

A fully bleached eucalyptus (cellulose pulp) fiber was introduced into a chamber which tapers upward from a 4-inch diameter at the base to a 6-inch diameter at the top of the main chamber. The unit has a perforated plate at the bottom serving as the distributor plate along with a spray nozzle is mounted at the center of the chamber. 100 grams of oven dried pulp fiber at an approximately 39 percent solid content and 30 grams of chitosan/HCA was fluidized in this chamber through adjustments to airflow in the distributor plate.

The inlet airflow was approximately 55 SCFM and 160° F. A mixture of Dow Corning® 84 (a silicone emulsion available from Dow Corning in Midland, Mich.) and titanium dioxide slurry (KEMIRA® UDR-P available from Kemira Pigment Co. In Savannah, Ga.), at a ratio of 35% silicone and 65% titanium dioxide based on solid content, was introduced through the nozzle and atomized into the chamber containing the fluidized fiber. The silicone emulsion was supplied to the nozzle at approximately 70° F. and approximately 5 percent as a water emulsion. The chitosan/HCA particles are smaller than 300 micrometer and larger than 100 micrometer and they were mixed with silicone emulsion and coated to the fiber surface. The air used to atomize the silicone emulsion was at approximately 1.1 SCFM. The fiber was coated by the silicone and chitosan/HCA and dried by the fluidization air. By adjusting the time the fiber was fluidized and the amount of the silicone applied, approximately 160 kg/(MT of fiber and chitosan/HCA) of silicone was coated on the fiber. The antimicrobiological testing results for various odor-producing bacteria are provided in Table 1. The antimicrobial testing was performed using Standard Test Method AATCC-100, by the American Association of Textile Chemists and Colorists. This method is incorporated by reference.

Example 2

This example relates to the coating of the same absorbent cellulose fibers used in Example 1, with an odor control system including citric acid and zinc oxide, using a silicone polymer binder.

The sample was prepared as Example 1 except that no chitosan/HCA was used. The coating solution was a mixture of 100 grams of citric acid, 64 grams of zinc oxide, 46 grams of Dow Corning® 84 Additives and 1800 grams water. The fiber was coated by the silicone and citric acid/zinc oxide and dried by the fluidization air. By adjusting the time the fiber was fluidized and the amount of the silicone applied, approximately 500 kg/MT silicone and citric acid/zinc oxide was coated on the fiber. The antimicrobiological testing results are provided in Table 1. Again, the antimicrobial testing was performed using AATCC-100.

Example 3

This example relates to the coating of activated carbon with the chitosan/HCA odor control system described in Example 1, using a silicone polymer binder.

Activated carbon was introduced into the chamber which tapers upward from a 4-inch diameter at the base to a 6-inch diameter at the top of the main chamber. The unit has a perforated plate at the bottom serving as the distributor plate along with a spray nozzle is mounted at the center of the chamber. 150 grams of activated carbon and 45 grams of chitosan/HCA was fluidized in this chamber through adjustments to airflow in the distributor plate. The inlet airflow was approximately 55 SCFM and 160° F. A mixture of Dow Corning® 36 (a silicone emulsion available from Dow Corning in Midland, Mich.) and titanium dioxide slurry (KEMIRA® UDR-P from Kemira Pigment Co. in Savannah, Ga.), at a ratio of 50% silicone and 50% titanium dioxide, was introduced through the nozzle and atomized into the chamber containing the fluidized material. The silicone emulsion was supplied to the nozzle at approximately 70° F. and approximately 20 percent solid content as a water emulsion. The air used to atomize the silicone emulsion was at approximately 1.1 SCFM. The carbon was coated by the silicone and chitosan/HCA and dried by the fluidization air. By adjusting the time the carbon was fluidized and the amount of the silicone applied, approximately 350 kg/(MT of fiber and chitosan/HCA) of silicone was coated on the carbon. The antimicrobiological testing results are provided in Table 1. Again, the antimicrobial testing was performed using AATCC-100.

TABLE 1

Antimicrobiological Testing results on CPI trial

Microbiological Testing Results

| | Code | Percent Reduction of Microorganism | | | | | |
|---|---|---|---|---|---|---|---|
| | Euc. Fiber- | E. Coli | P. Mirabillis | E. Cloacae | S. Aureus | C. Freundii | P. Retgerri |
| Fiber Control | control | NR | 41.94 | NR | NR | NR | NR |
| Example 1 | Euc. Fiber/Silicone/ Chitosan HCA | 47.48 | 91.3 | 99.92 | 94.44 | 46.67 | 99.95 |
| Example 2 | Euc. Fiber/Silicone/ Citric Acid & Zinc Oxide | 33.33 | 36.07 | 96.88 | 82.35 | 98.51 | 98.41 |
| Activated carbon control | Activated Carbon/ TiO2/Silicone- control | NR | NR | 14.29 | NR | NR | NR |
| Example 3 | Activated Carbon/ TiO2/Silicone/ Chitosan HCA (#7) | 70.31 | 18.64 | 61.25 | NR | NR | 38.13 |

NR = NO REDUCTION

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A treated fibrous material, comprising:
   a plurality of natural fibers;
   an odor control system on the fibers, the odor control system comprising a carboxylic acid-based odor control agent selected from multi-carboxylic acids, hydroxycarboxylic acids, chelating agents, and combinations thereof; and
   a binder on the fibers, the binder comprising an organosilicone polymer selected from poly(hexamethyldisiloxane), poly(octamethyltrisiloxane), poly(decamethyltetrasiloxane), poly(octamethylcyclotetrasiloxane), poly(octaphenylcyclotetrasiloxane), and combinations thereof.

2. The treated fibrous material of claim 1, wherein the natural fibers comprise cellulose fibers.

3. The treated fibrous material of claim 1, wherein the natural fibers comprise carbon fibers.

4. The treated fibrous material of claim 1, wherein the natural fibers comprise cellulose fibers and carbon fibers.

5. The treated fibrous material of claim 1, wherein the carboxylic acid-based odor control agent comprises a multi-carboxylic acid.

6. The treated fibrous material of claim 5, wherein the multi-carboxylic acid comprises a polymeric polycarboxylic acid.

7. The treated fibrous material of claim 1, wherein the carboxylic acid-based odor control agent comprises a hydroxycarboxylic acid odor control agent selected from citric acid, malic acid, tartaric acid, and combinations thereof.

8. The treated fibrous material of claim 1, wherein the carboxylic acid-based odor control agent comprises citric acid.

9. The treated fibrous material of claim 1, wherein the odor control system further comprises an odor control agent selected from chitin, chitosan, and combinations thereof.

10. The treated fibrous material of claim 1, wherein the odor control system further comprises a metal oxide.

11. The treated fibrous material of claim 1, wherein the odor control system further comprises an inorganic particulate material.

12. The treated fibrous material of claim 1, wherein the binder comprises a silicone polymer selected from the group consisting of liquid silicone polymers and silicone polymer emulsions.

13. A treated fibrous material, comprising:
    a plurality of absorbent fibers;
    about 0.1–50%, based on the weight of the absorbent fibers, of an odor control system comprising a multi-carboxylic acid-based odor control agent; and
    about 5–200 parts by weight of silicone polymer binder per 100 parts by weight of the odor control system.

14. The treated fibrous material of claim 13, comprising about 0.5–30% of the odor control system, based on the weight of the absorbent fibers.

15. The treated fibrous material of claim 13, comprising about 2–15% by weight of the odor control system, based on the weight of the absorbent fibers.

16. The treated fibrous material of claim 13, wherein the multi-carboxylic acid-based odor control agent comprises a hydroxycarboxylic acid.

17. The treated fibrous material of claim 13, wherein the multi-carboxylic acid-based odor control agent comprises a polymeric polycarboxylic acid.

18. The treated fibrous material of claim 13, wherein the multi-carboxylic acid-based odor control agent comprises citric acid.

19. The treated fibrous material of claim 13, wherein the odor control system further comprises chitin.

20. The treated fibrous material of claim 13, wherein the odor control system further comprises chitosan.

21. The treated fibrous material of claim 13, wherein the odor control system further comprises activated carbon.

22. The treated fibrous material of claim 13, wherein the odor control system further comprises a transition metal oxide.

23. The treated fibrous material of claim 13, comprising about 15–50 parts by weight of the silicone polymer binder per 100 parts by weight of the odor control system.

24. The treated fibrous material of claim 13, wherein the binder comprises a silicone polymer selected from liquid silicone polymers and silicone polymer emulsions.

25. A treated fibrous material, comprising:
   a plurality of cellulose fibers;
   an odor control system on the fibers, the odor control system comprising a hydroxycarboxylic acid and chitosan; and
   a binder on the fibers, the binder comprising an organosilicone polymer selected from poly(hexamethyldisiloxane), poly(octamethyltrisiloxane), poly(decamethyltetrasiloxane), poly(octamethylcyclotetrasiloxane), poly(octaphenylcyclotetrasiloxane), and combinations thereof.

26. A diaper comprising the treated fibrous material of claim 25.

27. Training pants comprising the treated fibrous material of claim 25.

28. Swim wear comprising the treated fibrous material of claim 25.

29. Absorbent underpants comprising the treated fibrous material of claim 25.

30. A baby wipe comprising the treated fibrous material of claim 25.

31. An adult incontinence product comprising the treated fibrous material of claim 25.

32. A feminine hygiene product comprising the treated fibrous material of claim 25.

33. A medical garment comprising the treated fibrous material of claim 25.

34. An underpad comprising the treated fibrous material of claim 25.

35. An absorbent drape comprising the treated fibrous material of claim 25.

36. A bandage comprising the treated fibrous material of claim 25.

37. A medical wipe comprising the treated fibrous material of claim 25.

38. A filter comprising the treated fibrous material of claim 25.

39. An industrial wipe comprising the treated fibrous material of claim 25.

40. A poultry pad comprising the treated fibrous material of claim 25.

41. A bed pad comprising the treated fibrous material of claim 25.

42. The treated fibrous material of claim 1, wherein the carboxylic acid-based odor control agent comprises a chelating agent.

43. The treated fibrous material of claim 13, wherein the multi-carboxylic acid-based odor control agent comprises a chelating agent.

* * * * *